(12) United States Patent
Johnson et al.

(10) Patent No.: US 7,468,073 B2
(45) Date of Patent: Dec. 23, 2008

(54) HEART VALVE SYSTEM

(75) Inventors: Keith M. Johnson, Coon Rapids, MN (US); Jack D. Lemmon, St. Louis Park, MN (US); Joseph C. Morrow, Eden Prairie, MN (US); Timothy R. Ryan, Shorewood, MN (US)

(73) Assignee: Medtronic, Inc., Minneapolis, MN (US)

( * ) Notice: Subject to any disclaimer, the term of this patent is extended or adjusted under 35 U.S.C. 154(b) by 149 days.

(21) Appl. No.: 11/401,800

(22) Filed: Apr. 11, 2006

(65) Prior Publication Data

US 2006/0195181 A1  Aug. 31, 2006

Related U.S. Application Data

(63) Continuation of application No. 10/131,933, filed on Apr. 25, 2002, now Pat. No. 7,189,258.

(60) Provisional application No. 60/345,297, filed on Jan. 2, 2002.

(51) Int. Cl.
*A61F 2/24* (2006.01)
(52) U.S. Cl. ..................................... 623/2.11
(58) Field of Classification Search .......... 623/2.1–2.39
See application file for complete search history.

(56) References Cited

U.S. PATENT DOCUMENTS

| | | |
|---|---|---|
| 3,099,016 A | 7/1963 | Edwards |
| 3,197,788 A | 8/1965 | Segger |
| 3,263,239 A | 8/1966 | Edwards et al. |
| 3,365,728 A | 1/1968 | Edwards et al. |
| 3,466,671 A | 9/1969 | Siposs |
| 3,509,582 A | 5/1970 | Pierie |
| 3,534,410 A | 10/1970 | Raible |
| 3,570,014 A | 3/1971 | Hancock |
| 3,656,185 A | 4/1972 | Carpentier |

(Continued)

FOREIGN PATENT DOCUMENTS

EP  0084395  8/1986

(Continued)

OTHER PUBLICATIONS

U.S. Appl. No. 60/117,445, filed Jan. 26, 1999, Carpentier et al.

(Continued)

*Primary Examiner*—Suzette J Gherbi
(74) *Attorney, Agent, or Firm*—Mike Jaro; Jeffrey J. Hohenshell

(57) ABSTRACT

A valve system including an aortic valve and a holder. The holder includes a holder body, which has a central portion, engagable with a holder handle, and downwardly extending leg portions that engage the valve in the areas between the commissure posts. The central portion of the holder further includes a spool located between the commissure posts, rotatable by an attached handle. Rotation of the spool draws in a tensile member passing through the commissure posts, drawing the commissure posts inward toward the spool. The tensile member passes through guides formed in the holder, configured such that they define the maximum available inward deflection of the commissure posts at the point at which the portions of the tensile member between the commissure posts assume straight configurations.

13 Claims, 6 Drawing Sheets

U.S. PATENT DOCUMENTS

| | | | |
|---|---|---|---|
| 3,710,744 A | 1/1973 | Goodenough et al. | |
| 3,714,671 A | 2/1973 | Edwards et al. | |
| 3,723,996 A | 4/1973 | Raible et al. | |
| 3,755,823 A | 9/1973 | Hancock | |
| 3,755,829 A | 9/1973 | Hancock | |
| 4,084,268 A | 4/1978 | Ionescu et al. | |
| 4,106,129 A | 8/1978 | Carpentier et al. | |
| 4,259,753 A | 4/1981 | Liotta et al. | |
| 4,291,420 A | 9/1981 | Reul | |
| 4,297,749 A | 11/1981 | Davis et al. | |
| 4,343,048 A | 8/1982 | Ross et al. | |
| 4,388,735 A | 6/1983 | Ionescu et al. | |
| 4,451,936 A | 6/1984 | Carpentier et al. | |
| 4,470,157 A | 9/1984 | Love | |
| 4,477,930 A * | 10/1984 | Totten et al. | 623/2.15 |
| 4,501,030 A | 2/1985 | Lane | |
| 4,626,255 A | 12/1986 | Reichart et al. | |
| 4,725,274 A | 2/1988 | Lane et al. | |
| 4,778,461 A | 10/1988 | Pietsch et al. | |
| 4,851,000 A | 7/1989 | Gupta | |
| 4,865,600 A | 9/1989 | Carpentier et al. | |
| 5,147,391 A | 9/1992 | Lane | |
| 5,163,953 A | 11/1992 | Vince | |
| 5,163,955 A | 11/1992 | Love et al. | |
| 5,258,023 A | 11/1993 | Reger | |
| 5,411,552 A | 5/1995 | Andersen et al. | |
| 5,449,384 A | 9/1995 | Johnson | |
| 5,476,510 A | 12/1995 | Eberhardt et al. | |
| 5,489,297 A | 2/1996 | Duran | |
| 5,489,298 A | 2/1996 | Love et al. | |
| 5,500,016 A | 3/1996 | Fisher | |
| 5,549,665 A | 8/1996 | Vesely et al. | |
| 5,554,185 A | 9/1996 | Block et al. | |
| 5,697,382 A | 12/1997 | Love et al. | |
| 5,702,368 A | 12/1997 | Stevens et al. | |
| 5,716,401 A | 2/1998 | Eberhardt et al. | |
| 5,716,417 A * | 2/1998 | Girard et al. | 623/2.38 |
| 5,728,152 A | 3/1998 | Mirsch, II et al. | |
| 5,800,527 A | 9/1998 | Jansen et al. | |
| 5,800,531 A | 9/1998 | Cosgrove et al. | |
| 5,855,601 A * | 1/1999 | Bessler et al. | 623/2.38 |
| 5,861,028 A | 1/1999 | Angell | |
| 5,895,420 A | 4/1999 | Mirsch, II et al. | |
| 5,928,281 A | 7/1999 | Huynh et al. | |
| 5,935,163 A | 8/1999 | Gabbay | |
| 5,964,770 A | 10/1999 | Flomenblit et al. | |
| 6,019,790 A | 2/2000 | Holmberg et al. | |
| 6,074,419 A | 6/2000 | Healy et al. | |
| 6,102,845 A | 8/2000 | Woodard et al. | |
| 6,338,740 B1 | 1/2002 | Carpentier | |
| 6,558,418 B2 | 5/2003 | Carpentier et al. | |
| 6,702,852 B2 | 3/2004 | Stobie et al. | |
| 6,736,845 B2 * | 5/2004 | Marquez et al. | 623/2.11 |
| 6,964,682 B2 | 11/2005 | Nguyen-Thien-Nhon et al. | |
| 6,966,925 B2 | 11/2005 | Stobie | |
| 7,018,407 B1 | 3/2006 | Wright et al. | |
| 7,033,390 B2 * | 4/2006 | Johnson et al. | 623/2.11 |
| 7,189,258 B2 * | 3/2007 | Johnson et al. | 623/2.11 |
| 2002/0082686 A1 | 6/2002 | Nguyen-Thien-Nhon | |
| 2004/0024451 A1 | 2/2004 | Johnson et al. | |
| 2004/0059413 A1 | 3/2004 | Argento | |
| 2004/0138741 A1 | 7/2004 | Stobie et al. | |
| 2004/0148017 A1 | 7/2004 | Stobie | |
| 2004/0148018 A1 | 7/2004 | Carpentier et al. | |
| 2006/0235510 A1 | 10/2006 | Johnson et al. | |

FOREIGN PATENT DOCUMENTS

| | | |
|---|---|---|
| EP | 0515324 | 12/1996 |
| GB | 2011259 A | 7/1979 |
| GB | 2108393 | 5/1983 |
| GB | 2279134 | 12/1994 |
| RU | 1806696 | 4/1993 |
| WO | 90/11738 | 10/1990 |
| WO | 92/12690 | 8/1992 |
| WO | 93/18721 | 9/1993 |
| WO | 95/28899 | 11/1995 |
| WO | 97/46177 | 12/1997 |
| WO | 98/43556 | 10/1998 |
| WO | 00/64382 | 4/1999 |
| WO | 00/00107 | 1/2000 |
| WO | 00/67661 | 11/2000 |
| WO | 02/49545 | 6/2002 |

OTHER PUBLICATIONS

Medtronic Brochure "A New Light on the Hancock™ Bioprosthesis" UC8801713EN 1988.

Medtronic Brochure "A New Dimension—The Hancock® II Bioprosthesis" UC9001297EN 1990.

Medtronic Brochure "The Hancock® Modified Orifice Bioprosthesis" UC9001297EN 1990.

Masterson, et al., "Universal Cardiac Valve Holder," Ann. Thor. Surg., Apr. 1977, p. 376.

Grismer, et al., "A Suture Holder and Separator Attachment to the Starr-Edwards Prosthetic Valve Holders," Surgery, Gynecology and Obstetrics, Mar. 1965, pp. 583-584.

Bernhard et al., "A 'Semi-Supported' Porcine Xenograft—Description and First Clinical Use," Thorac. Cardiovas. Surgeon 37 (1989) pp. 313-315.

Krucinski et al., "Numerical Simulation of Leaflet Flexure in Bioprosthetic Valves Mounted on Rigid and Expansile Stents," J. Biomechanics, vol. 26, No. 8 (1993) pp. 929-943.

Jansen, et al., "New J-3 flexible-leaflet polyurethane heart valve prosthesis with improved hydrodynamic performance," International Journal of Artificial Organs, vol. 14, No. 10 (1991) pp. 655-660.

Wright JM, et al., Hancock II—An Improved Bioprosthesis. In: cohn LJ, Glaucci V. ed. Cardiac Bioprostheses. New York, NY: New York Medical Books, 1982.

Hancock® II Bioprosthesis, Clinical Compendium, Copyright 2003, Medtronic, Inc.

Bortolotti et al., "Porcine Valve Durability: A Comparison Between Hancock Standard and Hancock II Bioprotheses," Ann. Thorac. Surg. 60:S216-20 (1995).

* cited by examiner

HEART VALVE SYSTEM

RELATED US APPLICATION DATA

This application is a continuation of U.S. patent application Ser. No. 10/131,933, filed Apr. 25, 2002, now U.S. Pat. No. 7,189,258 which application claims the benefit of Provisional U.S. Patent Application No. 60/345,297, filed Jan. 2, 2002 by Johnson, et al., incorporated herein by reference.

BACKGROUND OF THE INVENTION

This invention relates generally to the field of implantable valvular prostheses and more particularly to holding tools used for implantation of valvular prostheses.

To facilitate implantation of heart valve prostheses, various types of specialized holders have been developed. Such holders are intended to enable the implanting surgeon to precisely position the heart valve at its desired implant site and to securely hold the valve in place until suturing is complete. Some tools developed for use in conjunction with bioprosthetic or tissue heart valves have included a mechanism for causing inward deflection of the valves' commissure posts in order to facilitate the implantation procedure by improving the surgeon's access to the suture ring and host tissue disposed around the base of the replacement valve. One such holder, adapted for use in placing heart valves in the mitral position, is disclosed in U.S. Pat. No. 4,865,600 issued to Carpentier et al. Other such holders, adapted for use in placing valves in the aortic position, are disclosed in U.S. Pat. Nos. 5,716,401 and 5,476,510 issued to Eberhardt et al.

Medtronic Hancock® mitral valves are available mounted to a holder providing a mechanism for inward deflection, as illustrated in the brochures: "A New Dimension—The Hancock II Bioprosthesis", Medtronic Inc, 1991, publication number UC8903226EN and "A New Light on the Hancock Bioprosthesis", Medtronic, Inc., 1988, publication number UC8801713EN, both incorporated herein by reference in their entireties. This holder includes a ratcheting spool, mounted below the sewing ring, which when rotated by means of an attached handle, pulls lengths of suture inward, in turn pulling sutures extending upward though the commissure posts and between the commissure posts downward, to deflect the commissure posts inward.

SUMMARY OF THE INVENTION

The present invention describes a holder for use in conjunction with implantation of replacement aortic valves, especially smaller diameter valves. The holder is provided with a mechanism for causing inward deflection of the valve's commissure posts during the implantation procedure, and is optimized to protect the leaflets of the valve from damage during the implantation procedure. The holder is further designed to be located primarily between the commissure posts, rather than above them, further improving the surgeon's access.

The holder includes a holder body, which has a central portion, engagable with a holder handle, and three downwardly extending leg portions that engage the valve in the areas between the commissure posts, rather than engaging the commissure posts from above as in the above-cited Eberhardt, et al. patents. The central portion of the holder further includes a spool, rotatable by means of an attached handle, which serves to tighten a tensile member, such as a suture, passing through the commissure posts, drawing the commissure posts inward toward the spool. The spool is preferably located within a housing, from which the three legs descend. When attached to the valve, the housing is located centrally, between the tips of the commissure posts.

In a preferred embodiment, the tensile member passing through the commissure posts and coupled to the spool passes through guides formed in the downwardly extending leg portions of the holder. The guides are configured such that they define the maximum available inward deflection of the commissure posts at the point at which the portions of the suture extending between the guides assume straight configurations.

When the commissure posts are fully deflected inwardly, the descending legs of the holder fill up a substantial portion of the openings between the commissure posts, reducing the possibility of damage to the valve leaflets due to contact with the physician's fingers, needles or other surgical tools. The holder is released from the valve by cutting the sutures at one or more defined cut points to release the commissure posts from the suture attached to the spool and to release the legs of the holder from the portions of the valve prosthesis intermediate the commissure posts.

DETAILED DESCRIPTION OF THE PREFERRED EMBODIMENT

Figure 1:
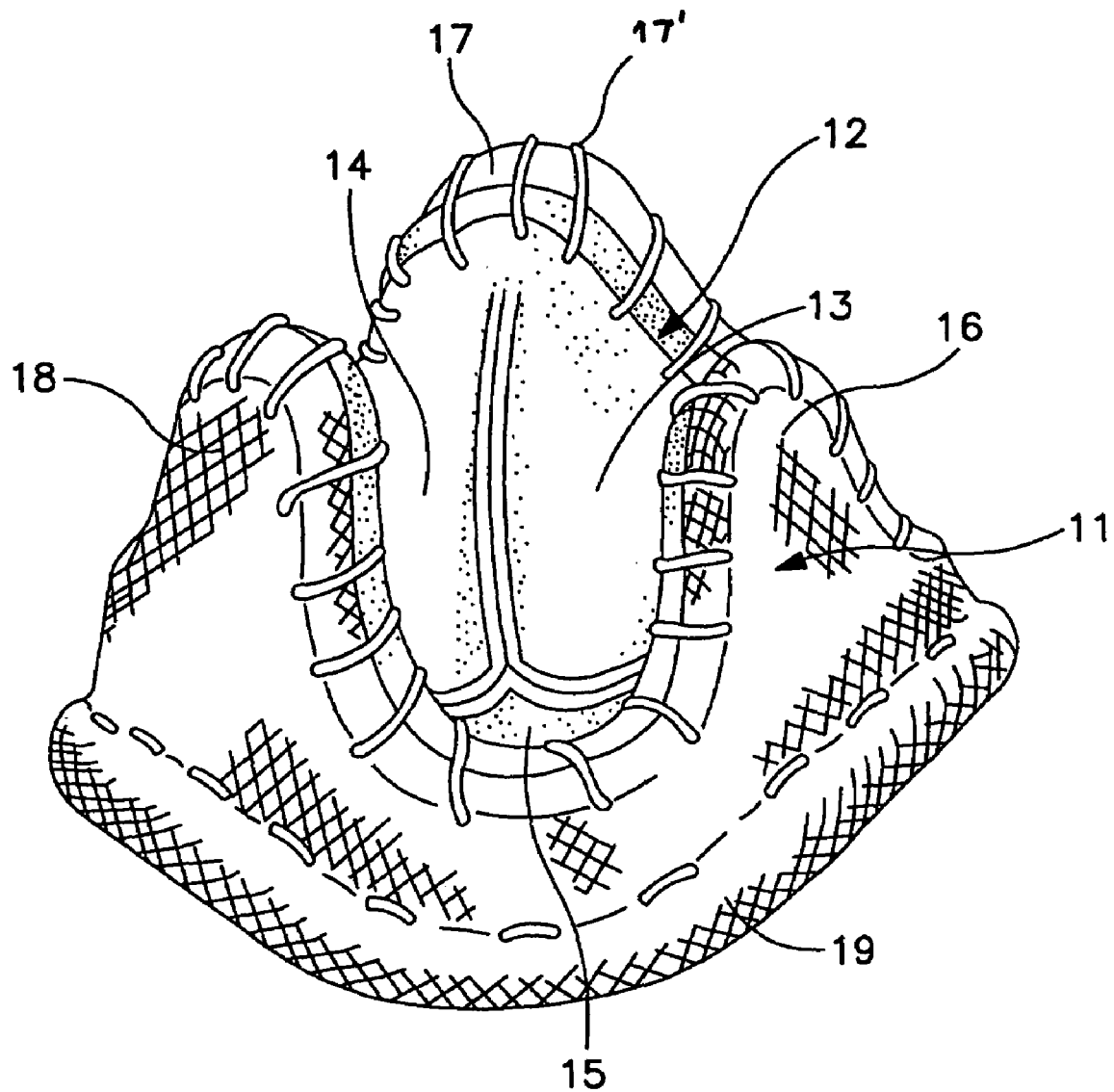
FIG. 1 is a perspective view of a prior art tissue valve of a type generally appropriate for use in conjunction with a holder according to the present invention

FIG. 1 is a perspective view of a prior art prosthetic heart valve of a type suitable for use in conjunction with the holder of the present invention. The valve includes a preserved porcine tissue valve mounted to a valve body, which includes a valve stent having three commissure posts 16, 17 and 18. The valve is provided with three flexible leaflets 13, 14 and 15, regulating flow of blood through the valve. The valve stent is covered with a fabric covering 11, and the fabric covering 11 and the valve 12 are secured to the stent by means of sutures 17'. A sewing ring or cuff 19 is provided at the lower end of the valve body, for use in attachment of the valve to the patient's valve annulus. While the valve illustrated in FIG. 1 is a bioprosthetic valve in which the leaflets 13, 14 and 15 take the form of preserved porcine heart valve leaflets, other types of similar valves are appropriate for use in conjunction with the present invention, including valves in which the leaflets are formed from pericardial tissue or synthetic materials, as described in U.S. Pat. No. 5,258,023 issued to Reger, U.S. Pat. No. 5,562,729 issued to Purdy, et al., U.S. Pat. No. 4,477,930 issued to Totten, et al. and U.S. Pat. No. 5,928,281 issued to Huynh, et al., all incorporated herein by reference in their entireties. Exemplary bioprosthetic valves are described in U.S. Pat. No. 5,935,163, issued to Gabbay, et al, U.S. Pat. No. 5,861,028 issued to Angell, U.S. Pat. No. 4,035,849 issued to Angell and U.S. Pat. No. 4,106,129 issued to Carpentier, also incorporated herein by reference in their entireties. In a particularly preferred application of the invention, it may be used in conjunction with the Medtronic Hancock series of bioprosthetic heart valves, as described in the Medtronic brochures discussed above brochures cited above.

Figure 2:
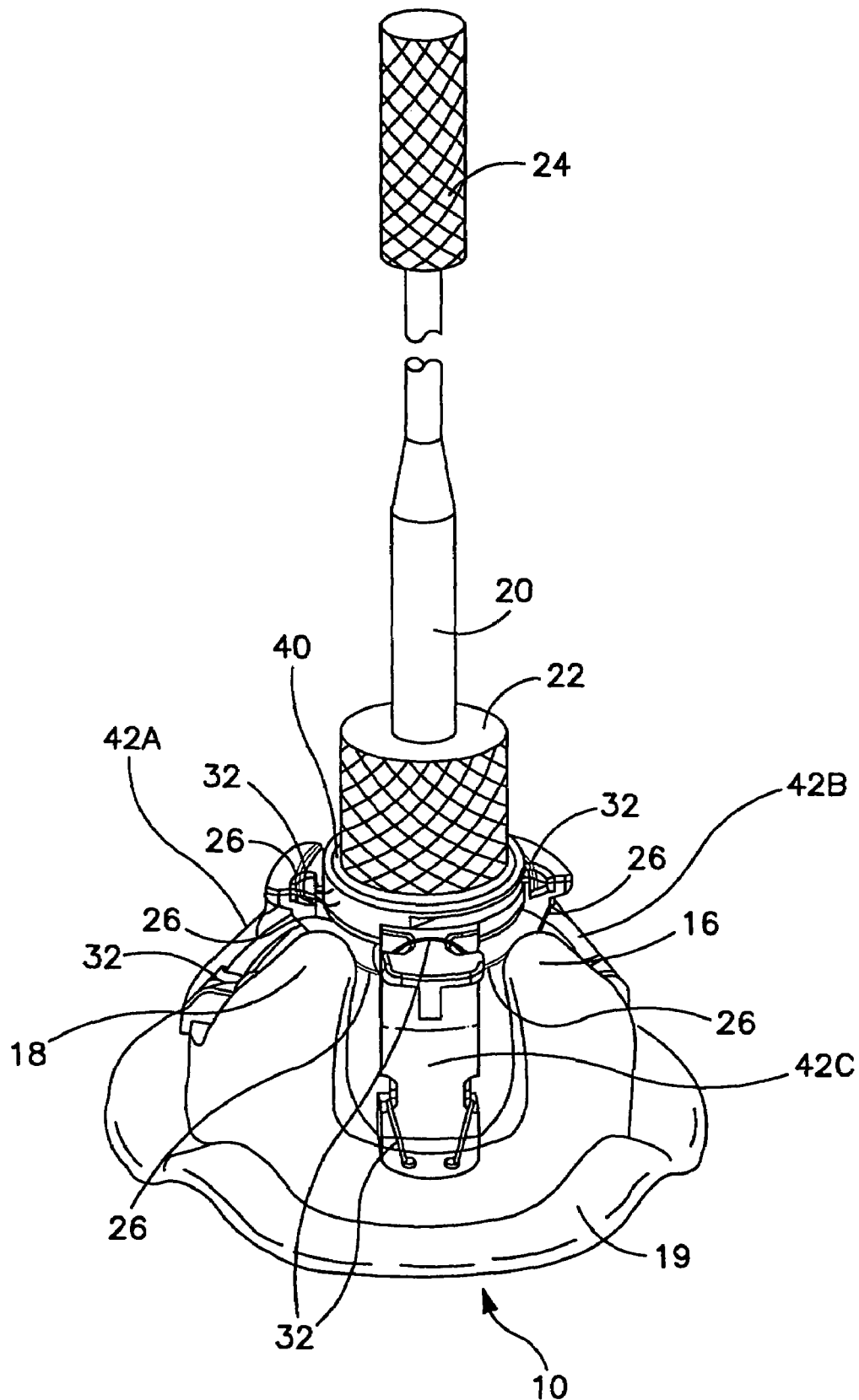
FIG. 2 is a holder according to the present invention, mounted to a handle and carrying a prosthetic heart valve.

FIG. 2 is a perspective view of a system comprising a holder according to the present invention, mounted to a handle 20 and carrying a bioprosthetic heart valve 10. The bioprosthetic heart valve 10, like the valve of FIG. 1 is mounted to a stent comprising three commissure posts 16, 17 and 18, extending upwardly from a sewing ring or cuff 19. The valve 10 also includes three flexible leaflets (not visible in this view) corresponding to leaflets 13, 14 and 15 of the valve of FIG. 1.

The holder includes a portion including a housing 40 from which three legs 42 A, B and C extend downwardly. Legs 42A, B and C are attached to the body of valve 10 in the valleys defined between the commissure posts 16, 17 and 18. The legs are coupled to the valve by means of sutures 32, the function of which is discussed in more detail in conjunction with FIG. 3 below. The upper ends or tips of the commissure posts 16, 17 and 18, as illustrated are deflected inwardly toward the housing 40 by means of a tension member 26 which passes through each of the commissure posts. Tension member 26 in the embodiment illustrated a length of suture material, but may be formed of other flexible cording material. An inner end of suture 26 is coupled to a rotatable spool located interior to housing 40 and coupled to handle 20. Rotation of handle 20 causes rotation of the spool in turn causing suture 26 to be wound around the spool and drawn inward, in turn causing and inward movement of the upper ends of the commissure posts 16, 17 and 18. This mechanism is discussed in more detail in conjunction with FIG. 3, below. Handle 20 terminates in a threaded rod that is screwed into the rotatable spool and extends upwardly to a narrowed handle 24. Handle 20 may also optionally be provided with a knurled lock nut 22, which locks the handle to the spool within the housing 40.

Figure 3:
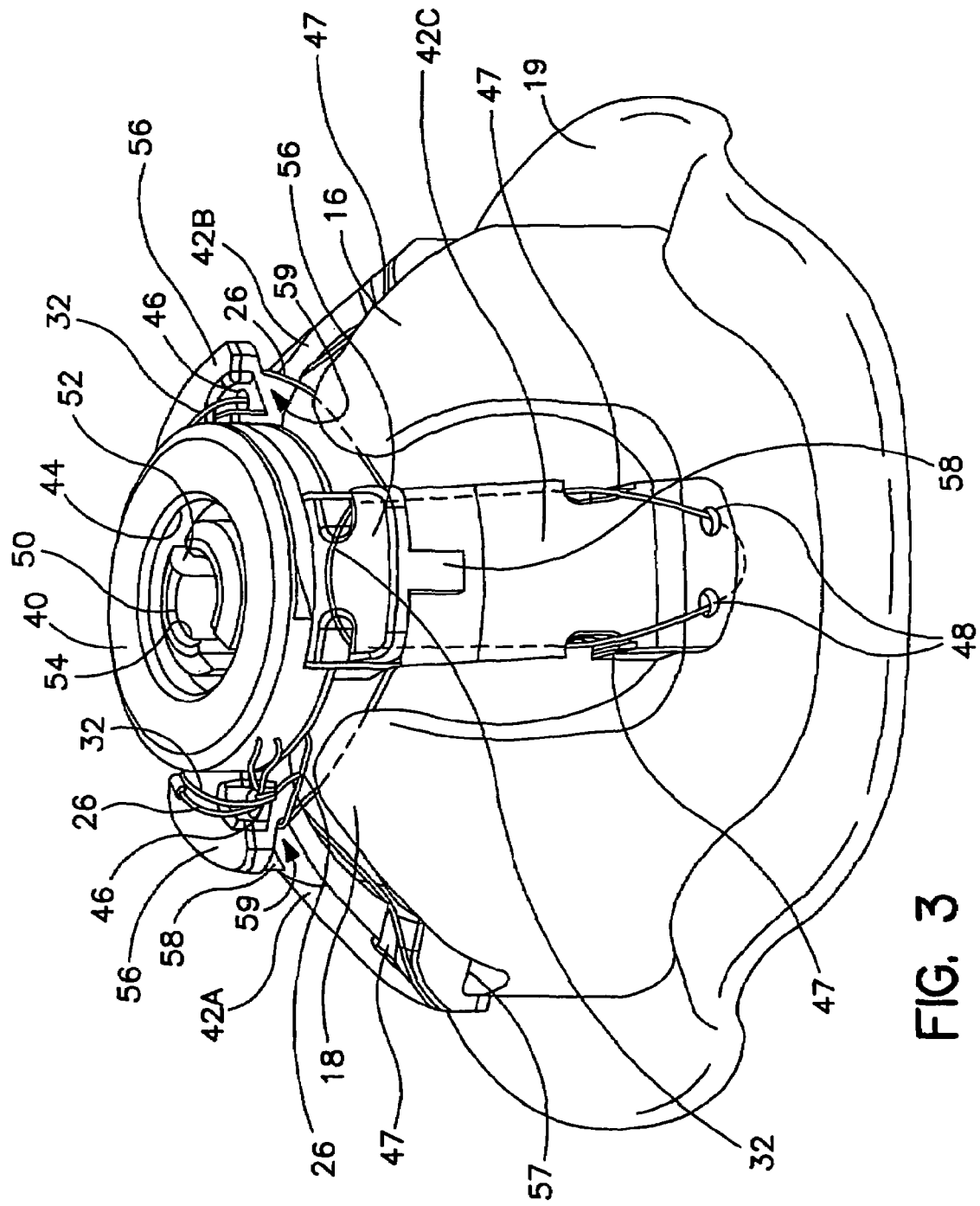
FIG. 3 is a perspective view of the valve and holder of FIG. 2, with the handle removed.

FIG. 3 is a perspective view of the valve and holder of FIG. 2 with the handle removed. In this view, the paths of the various sutures employed to hold the valve holder to the valve and to deflect the commissure posts inwardly are illustrated in broken line in those portions of the sutures paths not visible to the eye.

Figure 4:
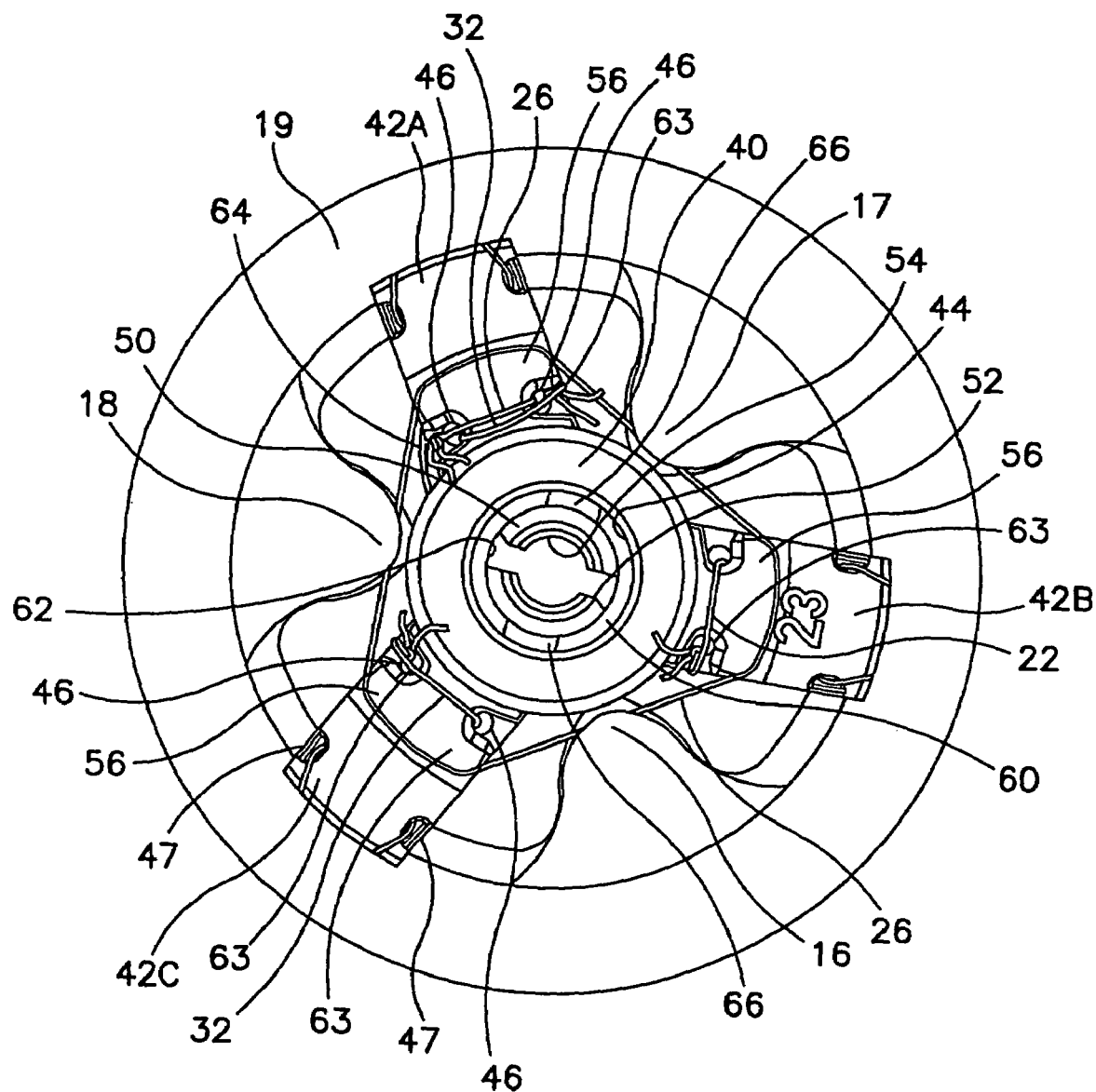
FIG. 4 is a top plan view of the valve and holder of FIG. 2.

In this view it can be seen that each of the downwardly extending legs 42A, B and C is provided with a suture or other cord-like retainer 32, which attaches the leg to the heart valve in one of the valleys defined between the commissure posts 16, 17 and 18. Each leg is provided with an outwardly extending flange 56, supported by a vertical support 58 and carrying two vertical bores or holes 46. Each suture 32 passes downward through one of the holes 46 on an outwardly extending flange 56, downwardly interior to the leg, through a lateral groove 47 to the exterior surface of the leg and then through a hole 48 in the leg, into the valve body. The suture then passes upwardly out of the valve body, through a second hole 48, upward through a second lateral groove 47, thereafter upward interior to the leg, through a second hole 46 and thereafter across the upper surface of flange 56 to the first hole 46. The ends of the suture 32 are both tied (to each other or to the holder) at the first of the holes 46 to anchor the suture to the holder. The knots in sutures 32 are illustrated in FIG. 4, below. To release the legs 42 A, B and C from the valve body, the sutures 32 are cut along those portions of the sutures extending across the tops of the laterally extending flanges 56. Different locations and/or numbers of cut points for sutures 32 may be substituted. In the embodiment illustrated, the structures of the legs 42 A, B and C, the sutures 32 and the associated holes, grooves and flanges are identical for all three legs.

The legs 42A, B and C extend from a central housing 40, which includes an upwardly opening orifice 44, in which the upper portion of a spool 50 is visible. The upwardly extending portion of the spool includes a threaded bore 54 and a crosswise slot 52, allowing the upper portion of the spool 50 to be compressed to facilitate its insertion into the housing 40. The lower portion of the spool, not visible in this view, is attached to the inner end of suture 26, which then extends outwardly and around the each of the three legs 42A, B and C along grooves or indentations 59 defined along the lower surfaces of respective ones of the flanges 56, through openings through the vertical supports 58 located beneath each of the flanges 56. The suture 26 passes through the upper portion of each of the commissure posts 16, 17 and 18, upward through a first hole 46 on Leg 42A, across the upper surface of flange 56 and finally is anchored to a second hole 46 in laterally extending flange 56. Rotation of the spool 50 causes the suture 26 to be drawn inward and causes corresponding inward motion of the commissure posts 16, 17 and 18 to assume the position illustrated.

To release the suture 26, it is cut along that portion of the suture extending across the top of the laterally extending flange 56 on leg 42A, typically concurrently with the cutting of suture 32 to release leg 42A from the valve body. In alternative embodiments, separate cut points may be defined for sutures 26 and 32, allowing release of suture 26 to allow the commissure posts to move outward without releasing the valve body from the holder. Also visible in this view is a notch 57, formed in the bottom of each of the legs 42 A, B and C, which rest on the upper surface of the valve body in the valleys between adjacent commissure posts.

A suture guide mechanism is provided, defining the maximum extent to which the suture can be wound around the spool and thereby defining the maximum inward deflection of the upper ends of the commissure posts 16, 17 and 18. The suture guides comprise the indentations 59 formed on the legs beneath the outwardly extending flanges 56 and the openings through the vertical supports 58. When the suture 26 is stretched tightly in straight segments between the suture guides, no further rotation of spool 50 is possible. The suture guides thereby also define the maximum point of inward deflection for the commissure posts 16, 17 and 18.

In use, the physician first attaches the handle 20 (FIG. 2) to the valve holder by means of a threaded rod at its lower end, which is screwed into the threaded recess 54 in spool 50. The knurled nut 22, (FIG. 2) if provided, is then rotated to lock the handle to the spool 50, so that rotation of the handle thereafter causes rotation of the spool and tightening of the suture 26, pulling the commissure posts 16, 17 and 18 inward until such time as the suture 26 assumes a generally straight configuration in areas between the legs 42 A, B and C, defining the point of maximum inward deflection. Sutures are placed through the valve annulus and then through the suture ring or cuff 19. The handle may optionally then be unscrewed from the holder. The sutures are then knotted to secure the valve to the valve annulus. The valve is then maneuvered to its desired location on or in the aortic valve annulus. After the valve is sutured and the knots are tied, the sutures 32 holding the holder to the valve and suture 26 are cut in those portions of the sutures extending across the tops of flanges 56 on legs 42 A, B and C. The valve holder can then be moved upward away from the valve, pulling the sutures, all of which remain anchored to the holder, through and out of the valve.

FIG. 4 is a top plan view of the holder and valve illustrated in FIG. 3. Numbered components in FIG. 4 correspond to identically numbered components in FIG. 3. In addition, in this view the knot 64 anchoring the outer end of the tension member 26 is visible, as are the knots 63 anchoring sutures 32 to the holder. Also visible in this view are outwardly extending projections 66, of spool 50. The upper end of spool 50 extends through a circular opening 62 formed in wall 60, defining the base of the upwardly opening recess 44 in housing 40. Slot 52 allows the upper end of spool 50 to be compressed, facilitating insertion of the spool through the circular opening 62. After re-expansion of the spool, projections 66 retain the spool within the housing 40.

Figure 5:
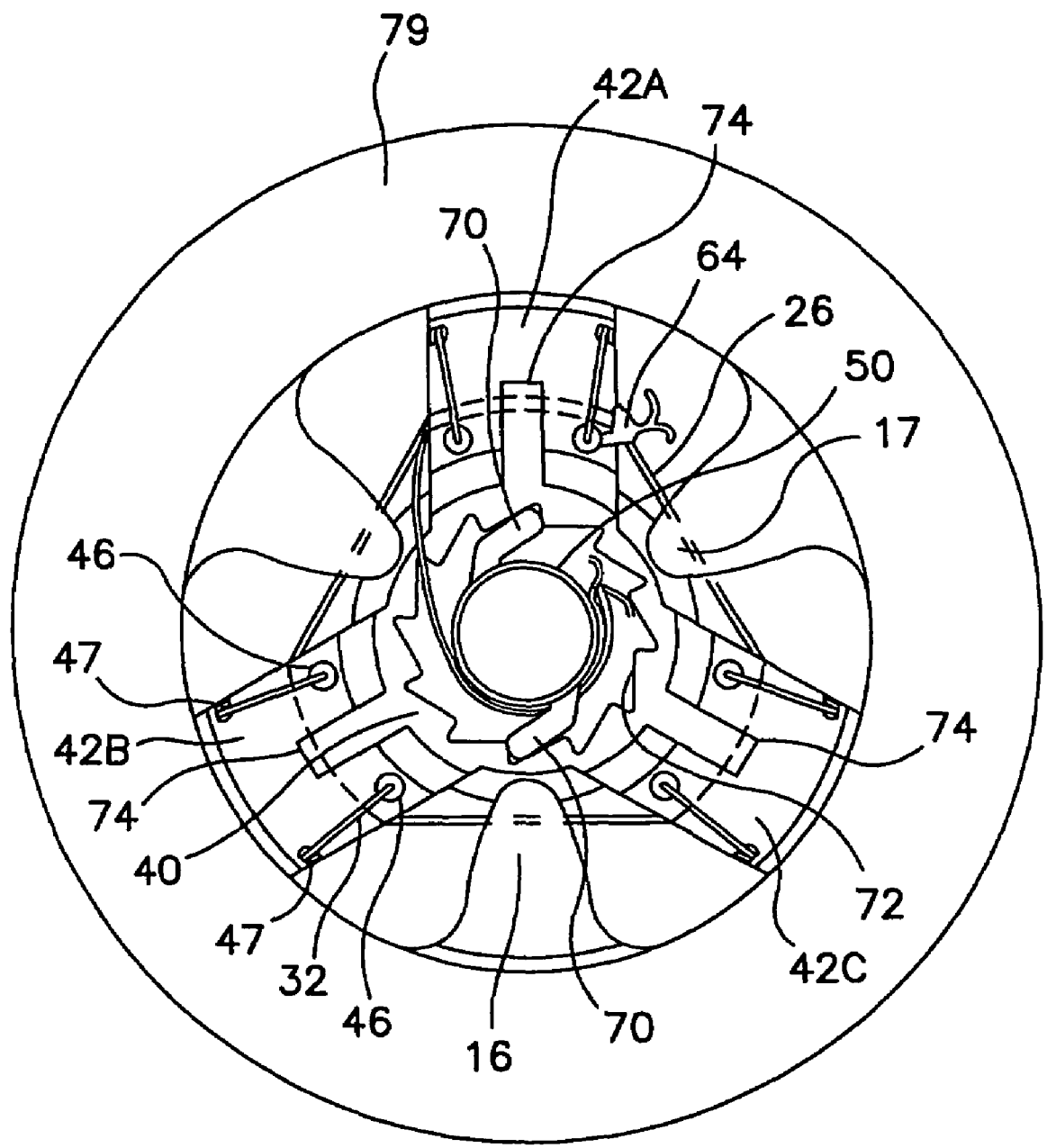
FIG. 5 is a bottom plan view of the valve and holder of FIG. 2.

FIG. 5 is a lower plan view of the holder and spool of FIG. 2. Numbered components of FIG. 5 correspond to identically numbered components of FIG. 2. The valve leaflets are omitted from the drawing to allow viewing of the lower portions of the spool 50 and housing 40, but as discussed above, correspond to those illustrated in FIG. 1. In this view it can additionally be seen that the lower portion of spool 50 is provided with two resilient outwardly directed arms 70, which engage in ramped recesses 72, formed in the lower surface of housing 40 to define a detent or ratchet. The ratchet allows rotation of the spool 50 only to wind the suture 26 around the spool and prevents unwinding of the suture 26 after pulling commissure posts 16, 17 and 18 inward. Also visible are the openings 74 in vertical supports 58 through which suture 26 passes.

Figure 6:
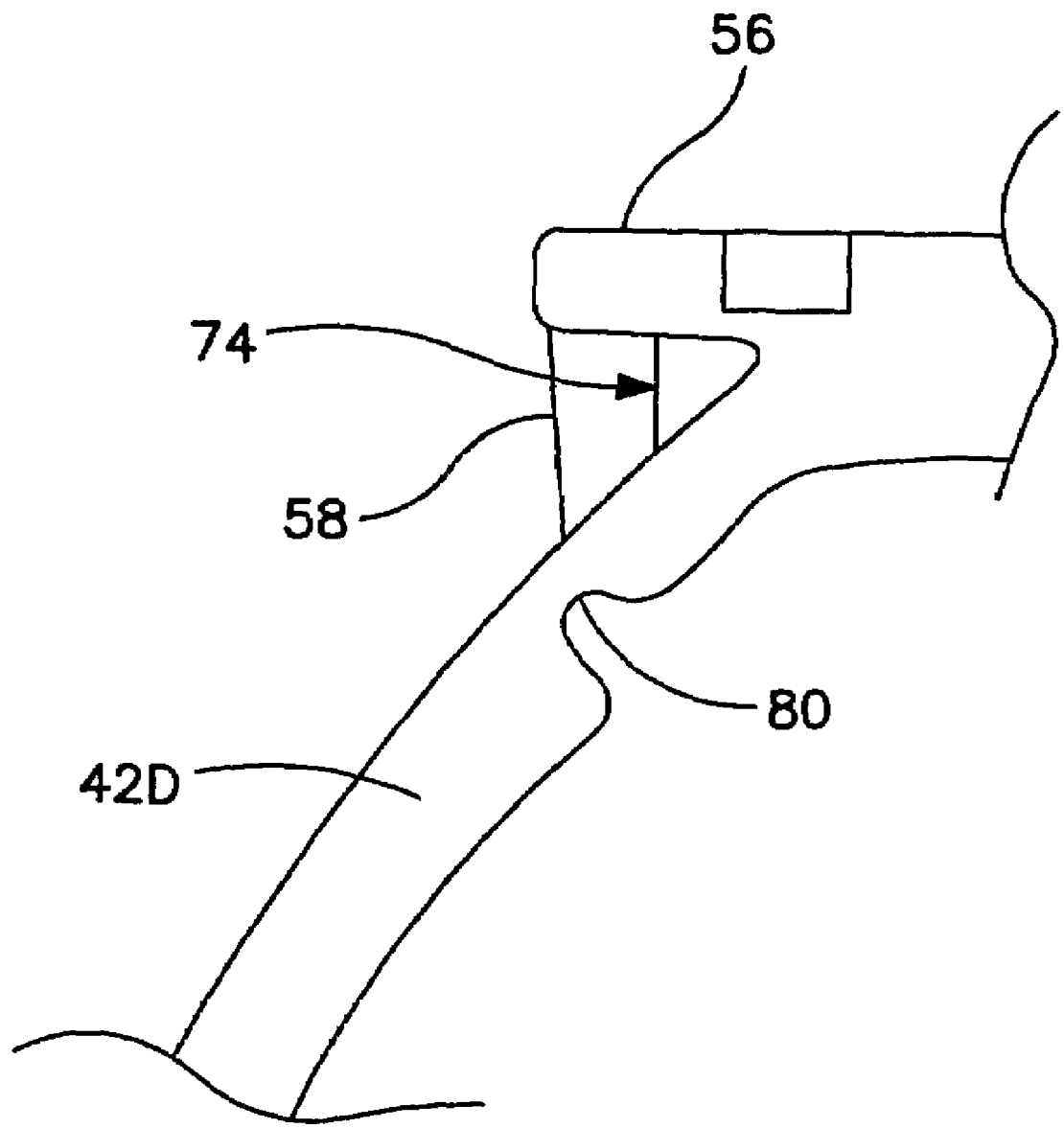
FIG. 6 is a side view of a portion of an alternative embodiment for a leg of a holder as in FIG. 2.

FIG. 6 is a partial side view of a portion of an alternative embodiment of a leg 42D which may be substituted for some or all of legs 42 A, B and C. Labeled components correspond to identically labeled elements in FIGS. 2-5, discussed above. Leg 42D corresponds structurally to legs 42 A, B and c, with the exception that it is additionally provided with a hinge or pivot 80, allowing it to move inward after removal of the holder from the valve body. Hinge 80 as shown is a molded or "living" hinge, however, alternative hinge designs can be substituted. The provision of hinges allows the holder to more easily be removed through small access incisions.

It should be noted that while the preferred embodiment of the valve holder according to the present invention includes a mechanism for producing inward deflection of the commissure posts, it is believed that a holder having the general configuration illustrated, e.g. a central portion having three downwardly extending legs adapted to engage the valve between the commissure posts is also useful in the context of a holder which does not include a mechanism for inward deflection of the commissure posts. Such a design retains the compact overall configuration of the holder as illustrated in the present application, improving the surgeon's access as compared to a holder mounted to the tips of the commissure posts as in the above cited Eberhardt patents. The placement of the downwardly extending legs between the commissure posts, even without inward deflection, also still serves to provide additional protection of the leaflets of the valve against inadvertent damage by the surgeon's fingers, needles or other surgical tools.

It should also be noted that while the preferred embodiment of the valve holder according to the present invention includes three downwardly extending legs adapted to engage the valve between the commissure posts, the placement of a spool mechanism for producing inward deflection of the commissure posts between the tips of the commissure posts is also believed valuable in conjunction with holders which engage the valve body at the tips of the commissure posts as in the prior art.

In conjunction with the above specification, we claim:

1. A bioprosthetic heart valve system, comprising: a heart valve comprising a valve body having a plurality of commissure posts extending to a first end of the valve body, each commissure post ending in a tip portion, a stent including a peripheral edge at a second end of the valve body, and a sewing ring that is spaced from the tip portions of the commissure posts and extending along the peripheral edge defining a ring structure at the second end of the valve body; and a holder having a holder body comprising a central portion engagable with a holder handle and having a plurality of legs extending downwardly from the central portion, releasably coupled to the valve body intermediate the commissure posts.

2. A system according to claim 1 wherein the central portion of the holder body is located between upper ends of the commissure posts.

3. A system according to claim 1 wherein the legs are coupled to the valve body by means of sutures.

4. A system according to claim 1, further comprising a holder handle, engaged with the central portion of the holder body.

5. A system according to claim 1, wherein at least one of the legs is provided with a hinge.

6. A system according to claim 1, wherein an opening at the second end of the valve body comprises an inflow end of the heart valve, which opening substantially maintains its size and shape during use as a heart valve after securing the sewing ring to an annulus of a heart.

7. A bioprosthetic heart valve system, comprising: a heart valve comprising a valve body having a plurality of commissure posts extending to a first end of the valve body, each commissure post ending in a tip portion, a stent including a peripheral edge at a second end of the valve body, and a sewing ring that is spaced from the tip portions of the commissure posts and extending along the peripheral edge defining a ring structure at the second end of the valve body; and a holder having a holder body comprising a central portion coupled to a holder handle and having a plurality of legs extending downwardly from the central portion, releasably coupled to the valve body intermediate the commissure posts.

8. A system according to claim 7 wherein the central portion of the holder body is located between upper ends of the commissure posts.

9. A system according to claim 7, wherein an opening at the second end of the valve body comprises an inflow end of the heart valve, which opening substantially maintains its size and shape during use as a heart valve after securing the sewing ring to an annulus of a heart.

10. A bioprosthetic heart valve system, comprising: a heart valve comprising a valve body having a plurality of commissure posts extending to a first end of the valve body, each commissure post ending in a tip portion, a stent including a peripheral edge at a second end of the valve body, and a sewing ring extending along the peripheral edge defining a ring structure at the second end of the valve body, wherein the tip portions of the commissure posts are free of any portion of the sewing ring; a holder having a holder body comprising a central portion engagable with a holder handle and having a plurality of legs extending downwardly from the central portion, releasably coupled to the valve body intermediate the commissure posts.

11. A system according to claim 10, wherein an opening at the second end of the valve body comprises an inflow end of the heart valve, which opening substantially maintains its size and shape during use as a heart valve after securing the sewing ring to an annulus of a heart.

12. A bioprosthetic heart valve system, comprising: a heart valve comprising a valve body having a plurality of commissure posts extending to a first end of the valve body, each commissure post ending in a tip portion, a stent including a peripheral edge at a second end of the valve body, and a sewing ring wherein the tip portions of the commissure posts are free of any portion of the sewing ring and extending along the peripheral edge defining a ring structure at the second end of the valve body; a holder having a holder body comprising a central portion coupled to a holder handle and having a plurality of legs extending downwardly from the central portion, releasably coupled to the valve body intermediate the commissure posts; and wherein the holder is spaced from the tip portions of the commissure posts.

13. A system according to claim 12, wherein an opening at the second end of the valve body comprises an inflow end of the heart valve, which opening substantially maintains its size and shape during use as a heart valve after securing the sewing ring to an annulus of a heart.

* * * * *

(12) INTER PARTES REEXAMINATION CERTIFICATE (1152nd)
United States Patent
Johnson et al.

(10) Number: US 7,468,073 C1
(45) Certificate Issued: Aug. 13, 2015

(54) HEART VALVE SYSTEM

(75) Inventors: Keith M. Johnson, Coon Rapids, MN (US); Jack D. Lemmon, St. Louis Park, MN (US); Joseph C. Morrow, Eden Prairie, MN (US); Timothy R. Ryan, Shorewood, MN (US)

(73) Assignee: MEDTRONIC, INC., Minneapolis, MN (US)

Reexamination Request:
No. 95/000,653, Dec. 17, 2011

Reexamination Certificate for:
Patent No.: 7,468,073
Issued: Dec. 23, 2008
Appl. No.: 11/401,800
Filed: Apr. 11, 2006

Related U.S. Application Data

(63) Continuation of application No. 10/131,933, filed on Apr. 25, 2002, now Pat. No. 7,189,258.

(60) Provisional application No. 60/345,297, filed on Jan. 2, 2002.

(51) Int. Cl.
*A61F 2/24* (2006.01)

(52) U.S. Cl.
CPC ............ *A61F 2/2439* (2013.01); *A61F 2/2412* (2013.01)

(58) Field of Classification Search
None
See application file for complete search history.

(56) References Cited

To view the complete listing of prior art documents cited during the proceeding for Reexamination Control Number 95/000,653, please refer to the USPTO's public Patent Application Information Retrieval (PAIR) system under the Display References tab.

*Primary Examiner* — Glenn K Dawson

(57) ABSTRACT

A valve system including an aortic valve and a holder. The holder includes a holder body, which has a central portion, engagable with a holder handle, and downwardly extending leg portions that engage the valve in the areas between the commissure posts. The central portion of the holder further includes a spool located between the commissure posts, rotatable by an attached handle. Rotation of the spool draws in a tensile member passing through the commissure posts, drawing the commissure posts inward toward the spool. The tensile member passes through guides formed in the holder, configured such that they define the maximum available inward deflection of the commissure posts at the point at which the portions of the tensile member between the commissure posts assume straight configurations.

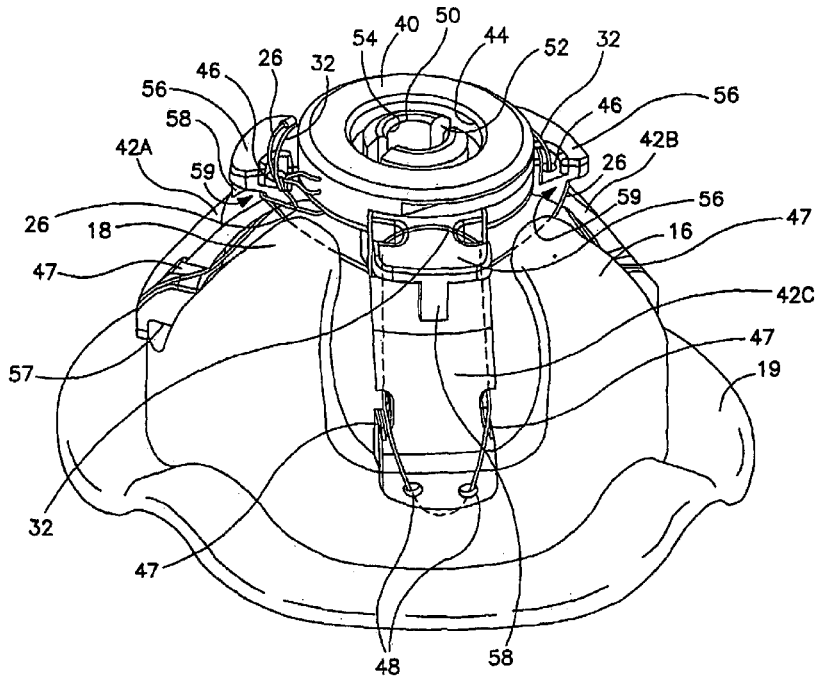

INTER PARTES REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1-4 and 6-13 are cancelled.

New claims 14-16 are added and determined to be patentable.

Claim 5 was not reexamined.

*14. A bioprosthetic heart valve system, comprising;*
*a heart valve comprising a valve body having a plurality of commissure posts extending to a first end of the valve body, each commissure post ending in a tip portion, a stent including a peripheral edge at a second end of the valve body, and a sewing ring that is spaced from the tip portions of the commissure posts and extending along the peripheral edge defining a ring structure at the second end of the valve body; and*
*a holder having a holder body comprising a central portion engagable with a holder handle and having a plurality of legs extending downwardly from the central portion, releasably coupled to the valve body via a suture passing through two holes in a distal end of a respective leg and looping through a portion of the valve body intermediate the commissure posts, the suture further wrapping around the respective leg such that the suture passes through the holes on an outside surface of the respective leg and wraps around to the inside surface of the leg at a region intermediate the distal end and a proximal end of the respective leg, the suture further passing over a groove on the proximal end of the respective leg to releasably secure the respective leg to the valve body.*

*15. A bioprosthetic heart valve system, comprising:*
*a heart valve comprising a valve body having a plurality of commissure posts extending to a first end of the valve body, each commissure post ending in a tip portion, a stent including a peripheral edge at a second end of the valve body, and a sewing ring extending along the peripheral edge defining a ring structure at the second end of the valve body,*
*wherein the tip portions of the commissure posts are free of any portion of the sewing ring;*
*a holder having a holder body comprising a central portion engagable with a holder handle and having a plurality of legs extending downwardly from the central portion, releasably coupled to the valve body via a suture intermediate the commissure posts, the suture passing through a first distal hole and a second distal hole of a respective leg and passing through a first proximal hole and a second proximal hole of the respective leg,*
*wherein a portion of the suture wraps around to the inside surface of the respective leg at a region intermediate the distal holes and the proximal holes.*

*16. A bioprosthetic heart valve system, comprising:*
*a heart valve comprising a valve body having a plurality of commissure posts extending to a first end of the valve body, each commissure post ending in a tip portion, a stent including a peripheral edge at a second end of the valve body, and a sewing ring wherein the tip portions of the commissure posts are free of any portion of the sewing ring and extending along the peripheral edge defining a ring structure at the second end of the valve body;*
*a holder having a holder body comprising a central portion coupled to a holder handle and having a plurality of legs extending downwardly from the central portion, releasably coupled to the valve body via a suture passing through a distal end of a respective leg intermediate the commissure posts, the suture further passing through a proximal end of the respective leg across an upper surface extending outwardly from the central portion,*
*wherein the holder is spaced from the tip portions of the commissure posts.*

\* \* \* \* \*